United States Patent
Sun et al.

(10) Patent No.: US 9,249,385 B1
(45) Date of Patent: Feb. 2, 2016

(54) SYSTEM AND METHOD FOR FUSING CELLS

(71) Applicant: City University of Hong Kong, Kowloon Tong (HK)

(72) Inventors: Dong Sun, New Territories (HK); Shuxun Chen, Kowloon Tong (HK); Ran Wang, Kowloon Tong (HK)

(73) Assignee: CITY UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 14/574,635

(22) Filed: Dec. 18, 2014

(51) Int. Cl.
*C12M 1/42* (2006.01)
*C12N 15/02* (2006.01)

(52) U.S. Cl.
CPC .............. *C12M 35/02* (2013.01); *C12N 15/02* (2013.01)

(58) Field of Classification Search
None
See application file for complete search history.

(56) References Cited

U.S. PATENT DOCUMENTS

| | | | |
|---|---|---|---|
| 4,822,470 A | 4/1989 | Chang | |
| 5,766,626 A | 6/1998 | Gross | |
| 6,863,406 B2 * | 3/2005 | Grier et al. | 359/614 |
| 8,426,205 B2 | 4/2013 | Eriksson et al. | |
| 2006/0281168 A1 | 12/2006 | Futami et al. | |
| 2008/0220431 A1 | 9/2008 | Yu | |
| 2010/0041103 A1 | 2/2010 | Gabbai | |
| 2010/0150931 A1 * | 6/2010 | Mourad et al. | 424/141.1 |
| 2013/0261049 A1 | 10/2013 | Desmet et al. | |
| 2013/0336939 A1 | 12/2013 | Podbilewicz et al. | |
| 2014/0044683 A1 | 2/2014 | Kitakaze et al. | |

FOREIGN PATENT DOCUMENTS

| | | |
|---|---|---|
| CA | 2458610 C | 3/2003 |
| CN | 1621516 A | 6/2005 |
| CN | 102876719 A | 1/2013 |
| CN | 102206580 B | 6/2013 |
| EP | 0251107 A3 | 1/1988 |
| EP | 1734111 A1 | 12/2006 |
| JP | 2006345706 A | 12/2006 |
| JP | 2007325586 A | 12/2007 |
| JP | 200854630 A | 3/2008 |
| JP | 2008259493 A | 10/2008 |
| JP | 2009124972 A | 6/2009 |
| JP | 2009254292 A | 11/2009 |
| JP | 201011824 A | 1/2010 |
| JP | 2011130728 A | 7/2011 |
| KR | 1020010005424 B1 | 1/2001 |
| KR | 1020130118080 A | 10/2013 |

OTHER PUBLICATIONS

Kuetemeyer et al., Femtosecond Laser-Induced Fusion of Nonadherent Cells and Two-Cell Porcine Embryos, Journal of Biomedical Optics vol. 16(8), Aug. 2011.
Gong et al., Femtosecond Laser-Induced Cell Fusion, Applied Physics Letters, 92, 2008.
He et al., All-Optical Human Cell Fusion by a Fiber Femtosecond Laser, American Institute of Physics, 93, 2008.
Steubing et al., Laser Induced Cell Fusion in Combination with Optical Tweezers: The Laser Cell Fusion Trap, Cytometry, 1991.
Wiegand et al., Laser-Induced Fusion of Mammalian Cells and Plant Protoplasts, Journal of Cell Science, 88, 1987.

* cited by examiner

*Primary Examiner* — Jim Ketter
(74) *Attorney, Agent, or Firm* — Heslin Rothenberg Farley & Mesiti P.C.; Melvin S. Li, Esq.

(57) ABSTRACT

The present invention is concerned with a system for fusion at least two cells. The system has an optical tweezers system for generating moving optical traps for manipulating the cells, an optical scissors system for cutting cell membrane of the cells and inducing fusion of the cells, an incubation system for providing cell culture in which the cells suspend and cell culture environment for the cells, and a visual detection system allowing visual monitoring of the cells undergoing fusion.

26 Claims, 6 Drawing Sheets

SYSTEM AND METHOD FOR FUSING CELLS

This patent application or patent file contains at least one drawing executed in color. Copies of this patent application or patent with color drawing(s) will be provided by the US Patent Office upon request and payment of the necessary fee.

FIELD OF THE INVENTION

The present invention is concerned with system and method for fusing biological cells together, in particular but not limited to producing multi-nucleate cells for experimental or clinical purpose.

BACKGROUND OF THE INVENTION

Manipulation of biological cells, including cell fusion, has a number of experimental or clinical applications. In the past, many methodologies for cell fusion make use of chemical or viral agents in achieving such fusion. However, which such methodologies are useful to some extent, they are deficient in that the chemical or viral agent would affect the end products, i.e. the fused cells, and ultimately affect the use of the fused cells in subsequent applications. Further, such methodologies often have been unreliable in controlling of fusion of specific number of cells or inefficient in that relative large amounts of pre-fused cells are required.

The present invention seeks to address these issues, or at least to provide an alternative to the public.

The present invention has many applications in the life science industry, and in particular in advanced biomedical device (e.g. for diseases diagnosis), drug discovery and laboratory research and tests. This invention allows the use of stem cells in many cellular biomedical applications, such as gene expression, chromosomal mapping, antibody production, cancer immunotherapy, and cell reprogramming. According to market research study conducted prior to the filing of the present invention, the global market for stem cell products was $3.8 billion in 2011, and it is expected to reach nearly $6.6 billion by 2016, increasing at a compound annual growth rate (CAGR) of 11.7% from 2011 to 2016. The global market for membrane technology reached $3.8 billion in 2010, nearly $4.6 billion in 2011, and is forecasted to reach $7.3 billion in 2016 after increasing at a compound annual growth rate (CAGR) of 9.9%. In view of these reasons, the present invention is technological advantageous.

SUMMARY OF THE INVENTION

According to a first aspect of the present invention, there is provided a system for fusion at least two cells, comprising an optical tweezers system for generation of a plurality of optical traps for manipulating the cells, an optical scissors system for cutting cell membrane of the cells and inducing fusion of the cells, an incubation system for providing cell culture in which the cells suspend and cell culture environment for the cells, and a visual detection system allowing visual monitoring of the cells undergoing fusion.

Preferably, the system may be free from using chemical factors, viral factors or antibiotics factors in inducing the fusion of the cells, or free from means to effect electro-fusion. With this arrangement, cell selectivity before cell fusion and cell viability after significantly improved. The system may be free of means to denature recognizing immunity system of reproducing cell pellicle, weaken or interfere the recognizing immunity function of reproducing cell.

The optical tweezers system may be a holographic optical tweezers system. The optical tweezers system may be configured to produce a continuous-wave laser source. The system may comprise means for splitting and steering single light beam into multiple beams. The means may include diffractive laser optical elements.

Suitably, the optical scissors system may be a pulsed UV laser system. The system may comprise a telescope for expanding pulsed laser beam from the pulsed UV laser system.

Advantageously, the incubation system may be a stage top incubation system including a stage top incubator provided with environment controls. The environment controls may include temperature control and Carbon dioxide ($CO_2$) concentration control.

In an embodiment, the vision detection system may include a microscope provided with a motorized stage, a light source and CCD camera. The vision detection system may be configured for bright-field imaging. Alternatively, the vision detection system may be configured for fluorescence imaging.

In one embodiment, the system may comprise a control system for controlling motion and position of a stage supporting the cells, controlling operation diffraction optical elements, and cutting frequency and time of optical scissors. The control system may be configured to control generation of one or more optical traps by the diffraction optical elements and movement of the one or more optical traps.

In a preferred embodiment, the system may comprise a container for containing the cells, bottom of the container being transparent at wavelength of lasers from the optical systems.

According to a second aspect of the present invention, there is provided a method of using a system as described above for fusing at least two cells together, comprising steps of manipulating the cells by using optical tweezers to form a cell pair or a cell chain shape, and fusing cell membrane of the cells by subjecting the cell membrane with pulsed UV laser.

According to a third aspect of the present invention, there is provided a method for fusing at least two cells together, comprising steps of manipulation of the cells by using optical tweezers to form a cell pair or a cell chain, and fusion of cell membrane of the cells by subjecting the cell membrane with pulsed UV laser. The method may comprise a step of generation of an optical trap for moving the cells close together or in contact with each other for forming the cell pair or cell chain. The manipulation may include controlling movement of motorized stage supporting the cells and position of the optical tweezers. The cells fused together may be a viable bi-nucleate or multi-nucleate cell. The cells before fusion may be in condition of suspended cells or adherent cells. The cells may include a stem cell and a somatic cell.

BRIEF DESCRIPTION OF DRAWINGS OF THE INVENTION

Some embodiments of the present invention will now be explained, with reference to the accompanied drawings, in which:—

Figure 1:
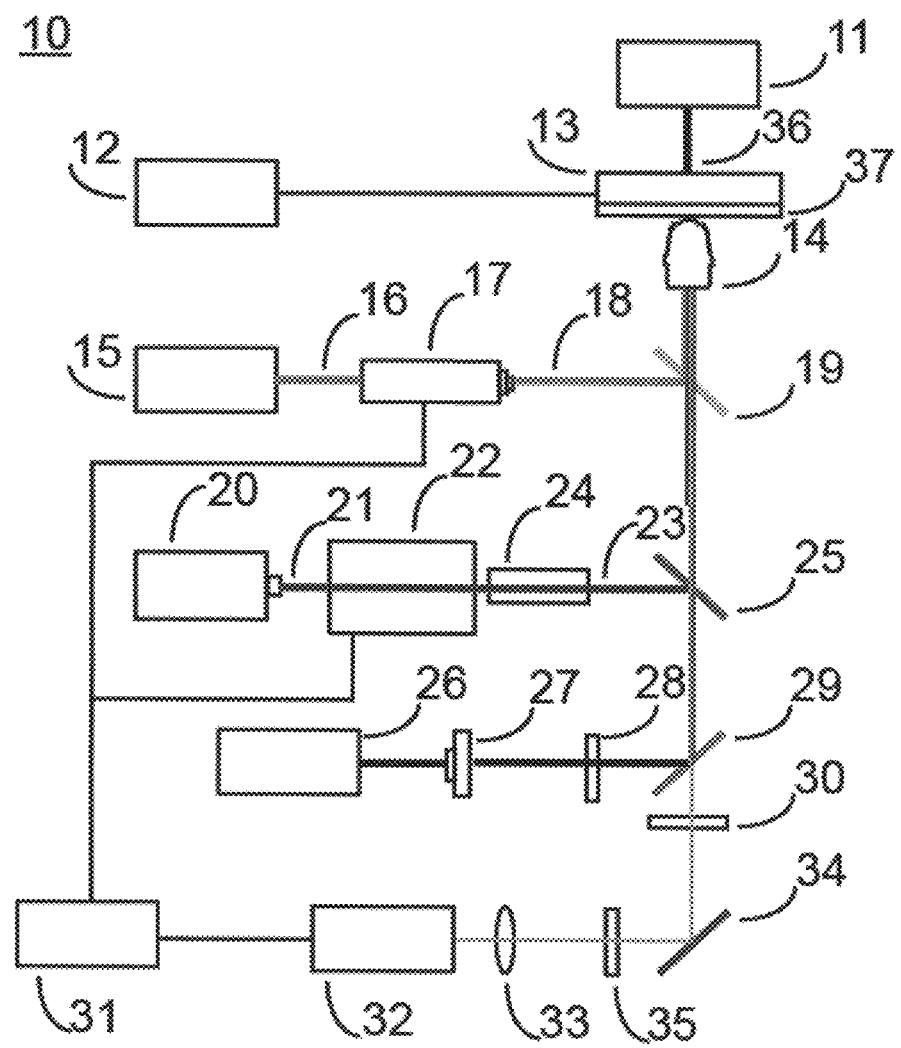
FIG. 1 is the schematic diagram showing an embodiment of a cell fusion system for manipulation of cells, the system comprised holographic optical tweezers and optical scissors.
Figure 4:
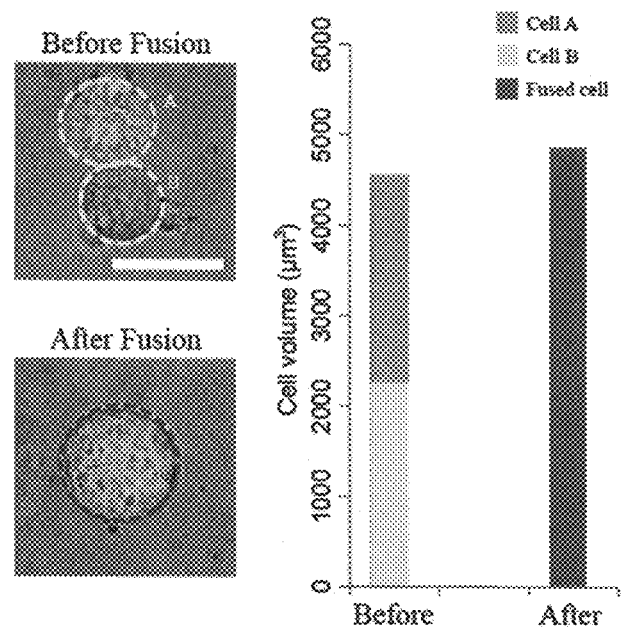
Figure 6:
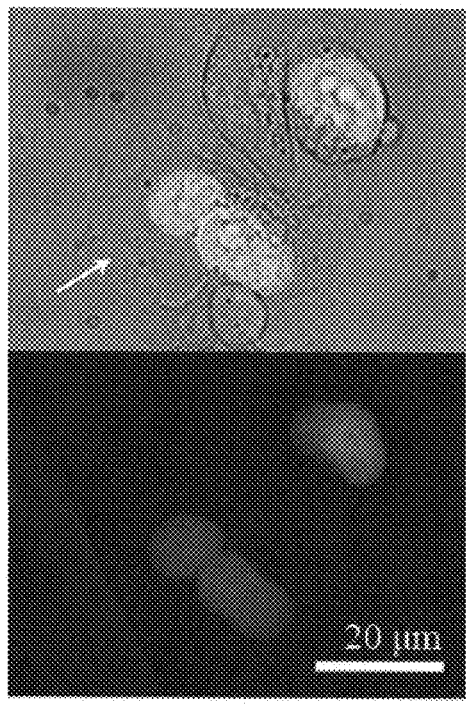

FIG. 4 includes photographic images showing cells before fusion and fused cell after fusion, and a graph showing change of cell volume of the cells before fusion and the fused cell after fusion;

FIGS. 5a-5e are a series of photographic images showing process of fusion of three cells using the system of FIG. 1;

FIG. 6 includes two photographic images showing a fused cell with two 2 nuclei;

FIGS. 7a-7d is are a series of photographic images showing a fused cell undergoing mitosis; and FIGS. 8a-8j are a series of photographic images showing fusion of a stem cell and a somatic cell by the system of FIG. 1.

DETAILED DESCRIPTION OF PREFERRED EMBODIMENTS OF THE INVENTION

The present invention provides system and method to artificially induce cell fusion at single-cell level. In particular, this invention makes use of laser induced cell fusion technology to generate viable multi-nucleated cell using for example stem cell as fusion partner. Laser fusion technology refers to the utilization of optical tweezers for manipulating two or more cells to form cell pair shape and the utilization of for example pulsed UV laser cutting for inducing cell fusion. Cell fusion refers to the merger of the selected cell membrane and mixing of cell cytoplasm in an aqueous environment without or with minimal cytoplasm leakage. Experiments on stem cell fusion are performed to demonstrate the effectiveness of the present invention. Laser-induced fusion between suspended or adherent cells can be achieved. Successful fusion of stem cell with somatic cell(s) is also demonstrated. This present invention is able to facilitate studies on cell differentiation, maturation, and reprogramming through cell fusion approach.

FIG. 1 is a schematic diagram showing an embodiment of a system for cell manipulation and cell fusion, generally designated 10. The system 10 comprises cell manipulation means and cell fusion means. In particular, the system comprises holographic optical tweezers and pulsed UV scissors which together allows fusion of two or more cells. The holographic optical tweezers apparatus produce a light source which, in this embodiment, is a continuous-wave laser source 15, which, in one preferred embodiment, is a laser source with a wavelength of 1064 nm. Laser beam 16 is sculpted by diffractive optical elements 17 to split and steer a single light of beam into multiple beams. In the holographic optical tweezers apparatus, the use of a spatial light modulator (SLM) is preferred and used in this embodiment. Sculpted laser beams 18 from the optical elements are reflected by a first dichroic mirror 19, and are transmitted into an inverted microscope objective 14. The inverted microscope objective 14 is used not only as means for providing function of the focusing of optical trap and optical scissors, it is also used as means for providing function of imaging of cell sample under operation. In order to ensure that the optical trap operates stably and reliable, the system makes use of objective lens with high or relatively high numerical aperture. The laser source of the optical scissors is pulsed laser source 20, which, in this embodiment, is a laser source with a wavelength of 355 nm. Pulsed laser beam 21 is expanded with a telescope 22 and then passed through an attenuator 24, which, in this embodiment, is a rotatable linear polarizer. Attenuated laser beam 23 is guided by a second dichroic mirror 25 and fulfills the back of inverted microscope objective 14.

The system 10 includes a stage top incubation arrangement. Subject cell samples under operation is placed in a stage top incubator 13, which, in this embodiment, is an environment-control chamber. An incubation controller 12 controls the temperature and $CO_2$ concentration inside the chamber 13. The stage top incubator 13 is located on a motorized stage 37.

The system 10 also comprises an optical imaging arrangement. In an operation in which bright-field imaging is used, illumination light 36 from an illuminator 11 provides optical radiation on the samples from top side (i.e. from above). In an operation in which fluorescence imaging is used, excitation light source 26 passes through a collimating adapter 27, through an excitation filter 28, and reflected by a third dichroic mirror 29. Transmitting through the second dichroic mirror 25 and the first dichroic mirror 19, the excitation light is focused on the sample by the inverted microscope objective 14. The excited fluorescence from the microscope objective 14 passes through all three dichroic mirrors, 19, 25, 29, through an emission filter 30, reflected by an optional mirror 34 to an optional filter 35 through an imaging lens 33 on a detector 32. The detector may be a CCD camera. A control system 31, which, in this embodiment, is a personal computer, can control motion or movement of the motorized stage 37. The control system 31 is configured to also control the diffractive optical elements 17 to generate one or more optical traps at the desired position and to control the movement of these traps. In addition, the control system can control the cutting frequency and cutting time of the optical scissors. The detector 32 captures live cell image and display on the control system 31.

Figure 2A:
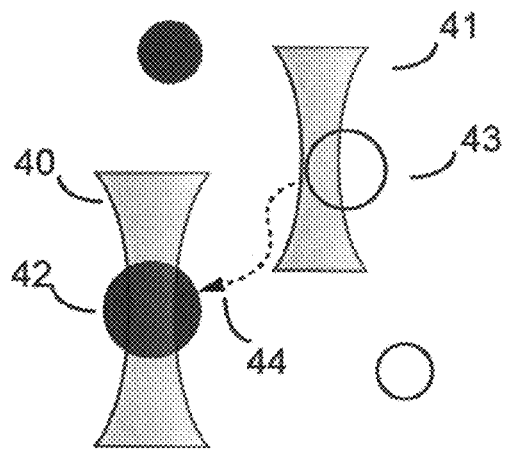
FIGS. 2a-2d are a series of diagram schematically illustrating a process of cell fusion using the system of FIG. 1.
Figure 2B:
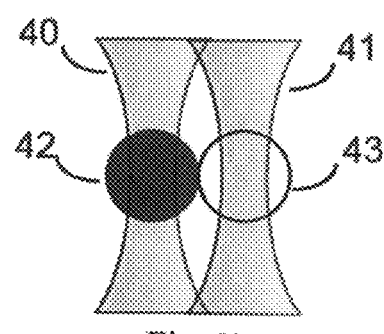
Figure 2C:
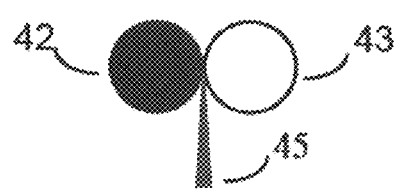
Figure 2D:
Figures 3A, 3B, 3C, 3D:
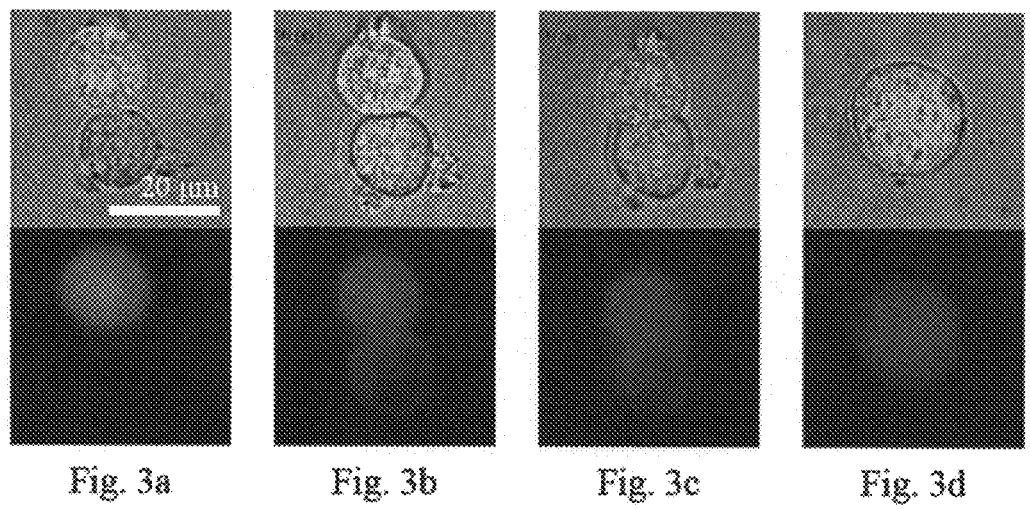
FIGS. 3a-3d are a series of photographic images showing by way of example the fusion of two suspended cells in a culture medium using the system of FIG. 1.

The use of optical tweezers and optical scissors requires that bottom wall of sample container be transparent at a wavelength of the laser beam used for cell trapping and fusion. Single cell sample can be obtained using enzymatic dissociation and put in a 35 mm culture dish with coverslip bottom. For fusion of cells of two cell types, the samples are the mixture of two kinds of cell, fluorescence labeled cells (such as fluorescence labeled cells) and unlabeled cells. A sample dish to support the samples is placed inside the stage top incubator 13. Adjusting the position of objective 14, the imaging plan is focused on the sample cells. It is to be noted that the detector, or the vision detector 32 captures the image and displays it on the control system 31. Please also FIGS. 2a-2d which illustrate operation principle of cell fusion of the present invention. FIG. 2a shows that by adjusting the motorized stage 37, a fluorescence labeled cell 42 is identified and an optical trap 40 is generated to trap the cell 42. A second trap 41 is generated to trap an unlabeled cell 43, and move the trapped cell following a predefined trajectory 44. Two trapped cells, 42 and 43, are manipulated by the two optical traps, 40 and 41, to form a cell pair shape, as shown in FIG. 2b. In order to move the two cells to contact each other, the power of the optical trap is increased. The cell pair of the cells 42, 43 is moved to a cutting spot of the scissors and then irradiated by the laser scissors, as shown in FIG. 2c. Laser pulse 45 is to be aimed at a precise area of contacting membranes at which the two cells are in contact. When fusion of the cells is successfully induced, a fused cell with fusion intermediate state 46 is observed. Please see FIG. 2d. Transfer of fluorescence from the fluorescence labeled cell to the unlabeled cell can be observed as the cells are being fusion successfully.

EXPERIMENTS

Experiment 1

FIGS. 3a-3d show a series of photographs of two-cell fusion subjected to an embodiment of cell fusion system as describe. A green florescent protein (GFP) labeled cell and an unlabeled cell were manipulated by two optical tweezers so that they moved towards each other and formed a cell pair. Please see FIG. 3a. After 5 pulses of laser cutting, the GFP inside the labeled cell were moving and transferring to the unlabeled cell, which indicates starting of cell fusion process. Please see FIG. 3b. As contract area of the membranes of the cells enlarged, mixing of cytoplasm from the two cells continued. The two cells gradually formed a single larger cell. Please see FIG. 3c. The fused cell gradually appeared round after fusion and became stale in that shape. The GFP inside the fused cell was then evenly distributed. These images illustrate that the present invention can be applied for suspended cell fusion.

Experiment 2

FIG. 4 shows the cell volume of the two cells before fusion and the fused cell after fusion. The volumes of Cells A and B were 2320 $\mu m^3$ and 2238 $\mu m^3$, respectively. The volumes of the fused cell at 30 min and 55 min after fusion were 5688 $\mu m^3$ and 4857 $\mu m^3$, respectively. The volume of the fused cell was 100% larger than Cell A or Cell B and approximated as the sum of the volumes of Cells A and B. Cell volume approximation before and after fusion confirmed that there was only minimal leakage of the cytoplasm occurred during laser-induced fusion, if at all.

Experiment 3

Figures 5A, 5B, 5C, 5D, 5E:
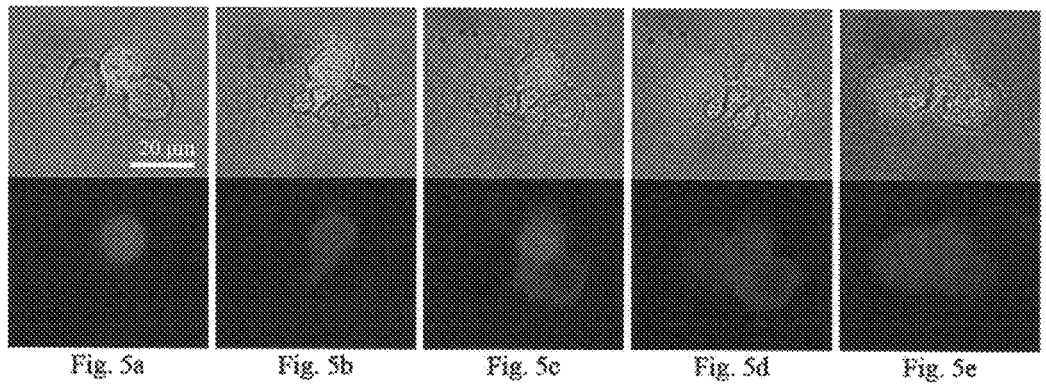

FIG. 5a-5e show a series of photographs of three-cell fusion effected by the system as described above. In this experiment, the entire fusion process took two main steps, firstly to fuse a first cell and a second cell to form an initially fused cell, and then to fuse the initially fused cell and a third cell to form a finally fused cell. FIG. 5a shows that three cells were manipulated by three optical tweezers forming a three-cell chain. One GFP labeled cell was selected and placed in the middle of the cell chain. As the sample was put inside the stage top incubator, cells naturally attached to the glass surface bottom and appeared cell morphology. Please see FIG. 5b. FIG. 5c shows that cell fusion was effected by the novel system of the present invention. It can be seen that fusion occurred with the labeled cell and the unlabeled cell on right side. FIG. 5d shows that the new generated fused cell was fused with the unlabeled cell on left side. All fusions were confirmed by GFP transferring from the labeled cell to unlabeled cell. Then the GFP became evenly distributed inside the fused cell. Please see FIG. 5e. These images illustrate that the present invention is applicable to fusion of multiple cells or adherent.

Experiment 4

FIG. 6 shows that a fused cell was produced by using the system as described above. The fused cell created after the fusion had two nuclei. This experiment demonstrates that the present invention can be applied to produce cells with multiple nuclei.

Experiment 5

Figure 7A:
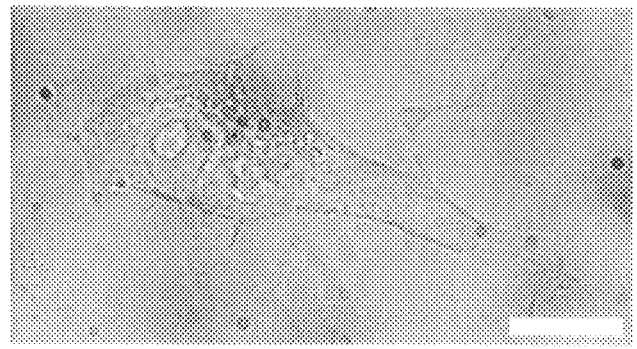
Figure 7B:
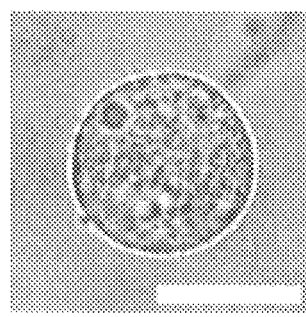
Figure 7C:
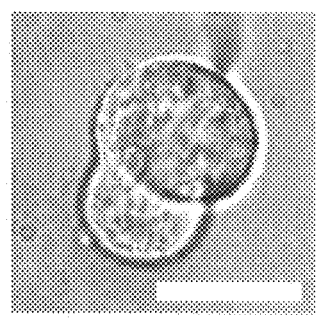
Figure 7D:
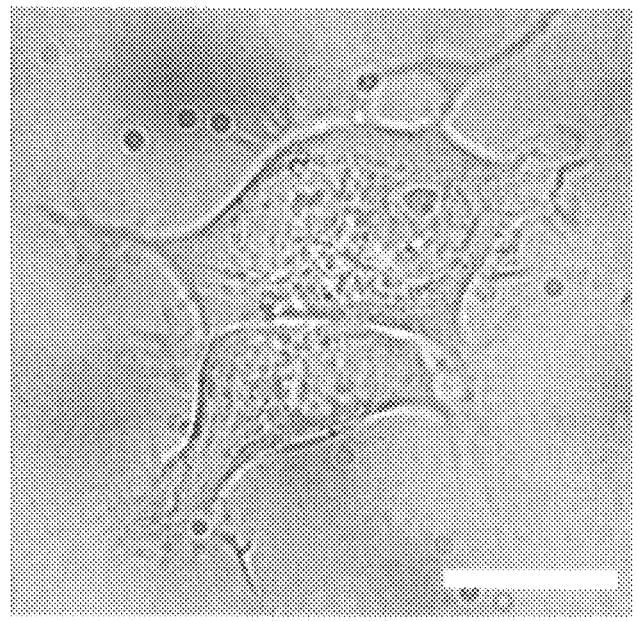
Figures 8A, 8B, 8C, 8D, 8E:
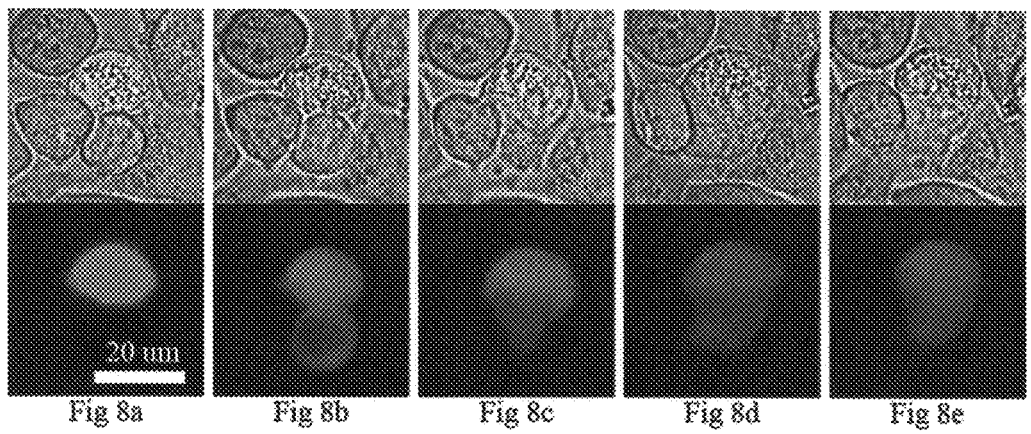
Figures 8F, 8G, 8H, 8I, 8J:
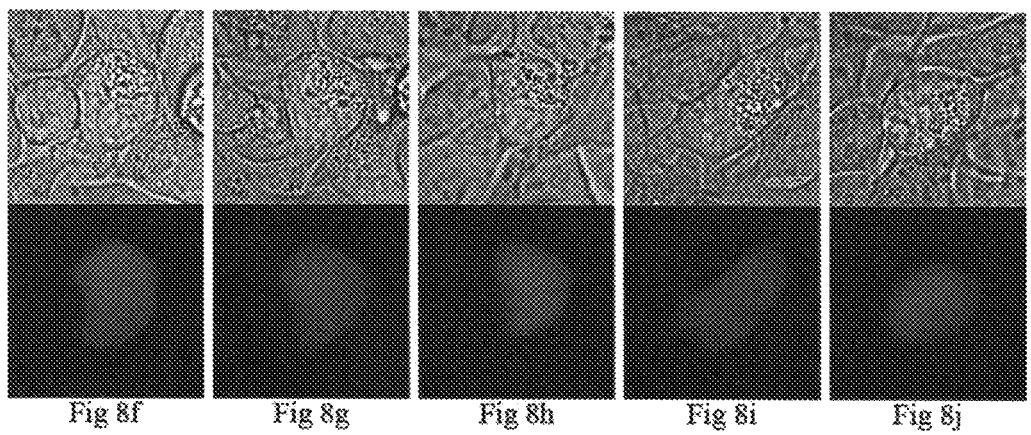

FIGS. 7a-7d show a series of photographs of a fused cell proceeding mitosis. Metaphase was observed 6 hours after cell fusion. Please see FIG. 7b. FIG. 7c is an image that shows the stage of the fusion process in telophase 40 min later. The fused cell gave rise to two daughter cells and started cytokinesis at 7 hours after cell fusion. Please see FIG. 7d. Mitosis verified the viability of the fused cell, indicating that the proposed invention could be implemented to generate viable fusion products.

Experiment 6

FIGS. 8a-8j show a series of time-lapse image of stem-somatic cell fusion. The somatic cells, human dermal fibroblasts (HDFn), were transfected with a pmCherry-C1 blank vector, expressing mCherry fluorescent protein (mCherry FP) driven by a human cytomegalovirus (hCMV) promoter. The mCherry FP-labeled HDFn were mixed with unlabeled stem cell immediately after enzymatic dissociation. After laser cutting of the membranes, the two cells started to fuse, as indicated by the transfer of the red fluorescence from mCherry FP labeled HDFn to the unlabeled stem cell. Please see FIG. 8b. The fusion was completed within approximately 10 min, and the fused cell attached to the cover glass exhibited morphology similar to surrounding cells. Please see FIG. 8e. The fused cell was completely attached to the surface of the coverslip and grew with surrounding stem cells as shown in FIGS. 8f-8j. These results demonstrated the effectiveness of the proposed invention in fusing stem cells with somatic cells.

The present invention is technically advantageous in a number of ways. The invention makes it possible for effecting single-cell fusion, which is particular suitable for fusion of rare cells, such as stem cells or primary cells. In contrast, conventional cell fusion methods, such as chemical induced and viral induced cell fusion, require large amounts of cells and cannot be implemented to single cell fusion. This is technically significant in cases where the quality of cell sample is limited.

The present invention also exhibits advantages of higher selectivity and controllability. It is to be appreciated that system and method of the present invention can choose particular or specific cells of interest for fusion, and this can significantly increase the degree of selectivity. The optical scissors are employed to induce fusion among target cells only, which improves the controllability of fusion process. As a result, the post-fusion cell selection process using antibiotics is not necessary. In contrast, conventional fusion methods often produce unwanted fusion products because they lack capabilities of selectivity and controllability.

This present invention is also advantageous in that it can enable cell fusion in physiological condition, e.g., cell culture medium and culture environment. Therefore, cell viability and cell function can be maintained, demonstrating that method of the invention is safer. This is to be contrasted with conventional fusion methods which often expose cells to be fused to hazardous substances, such as Sendai virus and PEG, which will bring the drawback of low cell viability, or would affect usability of the fused cells.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose. For example, a skilled person is considered to be aware the prior art listed below, the contents of this prior art is incorporated herein in their entirety.

1. CELL FUSION DEVICE, AND METHOD FOR CELL FUSION USING THE SAME (EP1734111; EP2270130)
2. CELL FUSION CHAMBER, CELL FUSION DEVICE, AND METHOD FOR CELL FUSION USING THE SAME (US20060281168; US20130011899; JP2007295912)
3. CELL FUSION APPARATUS AND CELL FUSION METHOD USING THE SAME (JP 2008259493; JP2008194029)
4. CELL FUSION VESSEL, CELL FUSION APPARATUS, AND METHOD FOR CELL FUSION USING THE SAME (JP2010011824)
5. CELL FUSION DEVICE AND CELL FUSION METHOD USING THE SAME (JP2008054630; JP2007295922)
6. MICROCHANNEL SUBSTRATE FOR CELL FUSION AND MICROCHANNEL STRUCTURE FOR CELL FUSION USING THE SAME AND CELL FUSION METHOD (JP2006345706)
7. DEVICE FOR CELL FUSION AND METHOD OF CELL FUSION BY USING THE SAME (JP2007325586)
8. A METHOD FOR SELECTIVE ELECTROFUSION OF AT LEAST TWO FUSION PARTNERS HAVING CELL-LIKE MEMBRANES (CA2380379; US20130052737; WO/2001/009297)
9. COMPOSITION AND METHOD FOR ENHANCING CELL GROWTH AND CELL FUSION (US20100041103; KR1020090106578; EP2121943)
10. METHOD OF AND APPARATUS FOR CELL PORATION AND CELL FUSION USING RADIOFREQUENCY ELECTRICAL PULSES (CA1340200; WO/1989/003426; U.S. Pat. No. 4,822,470; U.S. Pat. No. 5,304,486)
11. Cell fusion method (US20080220431; US20040148643)
12. CELL FUSION APPARATUS AND CELL FUSION METHOD (JP2009254292; JP2009273458)
13. METHOD FOR CONTROLLING CELL FUSION, VECTOR FOR GENE RECOMBINATION USED THEREFOR, AND CELL FUSION CONTROL AGENT (JP2009124972)
14. NON-LINEAR AMPLITUDE DIELECTROPHORESIS WAVEFORM FOR CELL FUSION (CA2458610; EP1472358)
15. IMPROVED FUSION PRODUCTS (EP0251107)
16. CELL FUSION METHOD FOR PRODUCTION OF SOMATIC CELL CLONED ANIMAL (KR1020010005424)
17. HYBRIDOMA, MONOCLONAL ANTIBODY, AND CELL FUSION METHOD (JP2011130728)
18. Electro-fusion method in somatic cell nuclear transfer (CN102876719)
19. Cell membrane fusion composition and method (U.S. Pat. No. 5,766,626; WO1995031183; U.S. Pat. No. 6,099,857)
20. Flow cytometry electrofusion apparatus (CN102206580)
21. Method for hybridization and fusion of organism germ cell and device thereof (CN1621516)
22. Cell fusion promoter and utilisation of the same (US20140044683)
23. Antinematodal methods and compositions (US20130336939)
24. Method for preparing induced pluripotent stem cells using intracellular protein transduction (KR1020130118080)
25. Alphabodies specifically binding to class-1 viral fusion proteins and method for pro ducting the same (US20130261049)
26. R. Wiegand, G. Weber, K. Zimmermann, S. Monajembashi, J. Wolfrum, and K. Greulich, "Laser-induced fusion of mammalian cells and plant protoplasts," *J Cell Sci*, vol. 88, pp. 145-149, Sep. 1, 1987 1987.
27. R. W. Steubing, S. Cheng, W. H. Wright, Y. Numajiri, and M. W. Berns, "Laser induced cell fusion in combination with optical tweezers: The laser cell fusion trap," *Cytometry*, vol. 12, pp. 505-510, 1991.
28. J. Gong, X. Zhao, Q. Xing, F. Li, H. Li, Y. Li, et al., "Femtosecond laser-induced cell fusion," *Applied Physics Letters*, vol. 92, p. 093901, 2008.
29. H. He, K. T. Chan, S. K. Kong, and R. K. Y. Lee, "All-optical human cell fusion by a fiber femtosecond laser," *Applied Physics Letters*, vol. 93, p. 163901, 2008.
30. K. Kuetemeyer, A. Lucas-Hahn, B. Petersen, H. Niemann, and A. Heisterkamp, "Femtosecond laser-induced fusion of nonadherent cells and two-cell porcine embryos," *Journal of Biomedical Optics*, vol. 16, pp. 088001-088001, 2011.

The invention claimed is:

1. A system for fusion at least two cells comprising:—
   a) an optical tweezers system for generation of a plurality of optical traps for manipulating the cells in isolation;
   b) an optical scissor system for cutting cell membrane of the cells and inducing fusion of the cells;
   c) an incubation system for providing cell culture in which the cells suspend and cell culture environment for the cells;
   d) a visual detection system allowing visual monitoring of the cells undergoing fusion; and
   e) a control system for controlling motion and position of a stage supporting the cells, controlling operation diffraction optical elements, and cutting frequency and time of optical scissors.

2. A system as claimed in claim 1, wherein said system is free from using chemical factors, viral factors or antibiotics factors, in inducing the fusion of the cells, or free from means to effect electro-fusion.

3. A system as claimed in claim 2, wherein said optical tweezers system is a holographic optical tweezers system.

4. A system as claimed in claim 2, wherein said optical tweezers system is configured to produce a continuous-wave laser source.

5. A system as claimed in claim 2, comprising means for splitting and steering single light beam into multiple beams.

6. A system as claimed in claim 5, wherein said means includes diffractive laser optical elements.

7. A system as claimed in claim 2, wherein said optical scissor system is a pulsed UV laser system.

8. A system as claimed in claim 7, comprising a telescope for expanding pulsed laser beam from said pulsed UV laser system.

9. A system as claimed in claim 2, wherein said incubation system is a stage top incubation system including a stage top incubator provided with environment controls.

10. A system as claimed in claim 5, wherein said environment controls include temperature control and carbon dioxide ($CO_2$) concentration control.

11. A system as claimed in claim 1, wherein said vision detection system includes a microscope provided with a motorized stage, a light source and CCD camera.

12. A system as claimed in claim 11, wherein said vision detection system is configured for bright-field imaging.

13. A system as claimed in claim 11, wherein said vision detection system is configured for fluorescence imaging.

14. A system as claimed in claim 8, wherein the UV laser system is adapted to deliver pulsed UV laser of substantially 355 nm in wavelength.

15. A system as claimed in claim 1, wherein said control system is configured to control generation of one or more optical traps by said diffraction optical elements and movement of said one or more optical traps.

16. A system as claimed in claim 1, comprising a container for containing the cells, bottom of said container being transparent at wavelength of lasers from said optical systems.

17. A method of using a system as claimed in claim 1 for fusing at least two cells together, comprising:—
   a) manipulating the cells by using optical tweezers to form a cell pair or a cell chain shape; and
   b) fusing cell membrane of the cells by subjecting the cell membrane with pulsed UV laser.

18. A method for fusing at least two cells together, comprising:—
   a) manipulation of the cells by using optical tweezers to form a cell pair or a cell chain; and
   b) fusion of cell membrane of the cells by subjecting the cell membrane with pulsed UV laser;
   wherein said manipulation includes controlling movement of motorized stage supporting the cells and position of said optical tweezers.

19. A method as claimed in claim 18, comprising generation of an optical trap for moving the cells close together or in contact with each other for forming the cell pair or cell chain.

20. A method as claimed in claim 18, wherein the cells fused together is a viable bi-nucleate or multi-nucleate cell.

21. A method as claimed in claim 18, wherein the cells before fusion are in condition of suspended cells or adherent cells.

22. A method as claimed in claim 18, wherein the cells include a stem cell and a somatic cell.

23. A method as claimed in claim 17, comprising generation of an optical trap for moving the cells close together or in contact with each other for forming the cell pair or cell chain.

24. A method as claimed in claim 17, wherein the cells fused together is a viable bi-nucleate or multi-nucleate cell.

25. A method as claimed in claim 17, wherein the cells before fusion are in condition of suspended cells or adherent cells.

26. A method as claimed in claim 17, wherein the cells include a stem cell and a somatic cell.

* * * * *